United States Patent [19]

Umezawa, deceased et al.

[11] Patent Number: 4,925,877

[45] Date of Patent: * May 15, 1990

[54] PHYSIOLOGICALLY ACTIVE ERBSTATIN ANALOGUE COMPOUNDS AND COMPOSITIONS

[75] Inventors: Hamao Umezawa, deceased, late of Tokyo, by Mieko Umezawa, Kazuo Umezawa, Yoji Umezawa, heirs; Tomio Takeuchi; Kuniaki Tatsuta, both of Tokyo; Kunio Isshika, Fujisawa; Masaya Imoto, Tokyo, all of Japan

[73] Assignee: Zaidanhojin Biseibutsu Kagaku Kenkyukai, Tokyo, Japan

[ * ] Notice: The portion of the term of this patent subsequent to Aug. 11, 2004 has been disclaimed.

[21] Appl. No.: 17,108

[22] Filed: Feb. 20, 1987

[30] Foreign Application Priority Data

Feb. 25, 1986 [JP] Japan ................................. 61-39382
Apr. 8, 1986 [JP] Japan ................................. 61-81522

[51] Int. Cl.$^5$ .................... A61K 31/165; C07C 103/38
[52] U.S. Cl. ...................................... 514/630; 564/219
[58] Field of Search ........................ 564/219; 514/630

[56] References Cited

U.S. PATENT DOCUMENTS

| | | | |
|---|---|---|---|
| 3,689,557 | 9/1972 | McCaully et al. | 260/559 B |
| 3,944,675 | 3/1976 | Symchowicz et al. | 424/324 |
| 4,053,509 | 10/1977 | Faro et al. | 260/557 R |
| 4,686,308 | 8/1987 | Umezawa et al. | 564/219 |

FOREIGN PATENT DOCUMENTS

1225357 3/1971 United Kingdom .

OTHER PUBLICATIONS

Wick et al., I, Chem. Abst., (1981), vol. 94, p. 52, 150252(p).

Wick et al., II, Chem. Abst., (1979), vol. 91, p. 40, 186573(w).
Umehara et al., Chem. Abst., (1984), vol. 101, p. 325, 87029(s).
Umezawa et al., II, J. of Antibiotics, (1986), vol. 39, pp. 170-173.

Primary Examiner—Glennon H. Hollrah
Assistant Examiner—Peter G. O'Sullivan
Attorney, Agent, or Firm—Jordan and Hamburg

[57] ABSTRACT

The present invention provides new physiological active substance erbstatin analogue compounds of a general formula (I), which have excellent tyrosine-specific protein-kinase inhibitory activity, antitumor activity and antimicrobial activity.

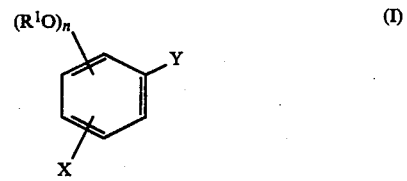

(in which $R^1$ represents a hydrogen atom, a lower alkanoyl group or a lower alkyl group; n represents a positive integer of 1 to 3;
  X represents a hydrogen atom or a halogen atom;
  Y represents a group of formula —CH=CH—NC, —CH=CH—NHR$^2$ or —CH$_2$—CH$_2$—NHR$^2$
  (where $R^2$ represents a formyl group or a lower alkanoyl group; with the exception of the cases where X is hydrogen atom, (R$^1$O)$_n$ group is 2,5-dihydroxy group and Y is —CH=CH—NHCHO or —CH$_2$—CH$_2$—NHCHO).

The present invention further provides a tyrosine-specific protein-kinase inhibitor, tumoricide or bactericide containing at least one compound of the said formula (I).

2 Claims, No Drawings

PHYSIOLOGICALLY ACTIVE ERBSTATIN ANALOGUE COMPOUNDS AND COMPOSITIONS

FIELD OF THE INVENTION

The present invention relates to new physiological active substances, more concretely, to those having tyrosine-specific protein-kinase inhibitor activity, antitumor activity and antimicrobial activity.

BACKGROUND OF THE INVENTION

Regarding antitumor substances, a lot of compounds have heretofore been put to practical use as medicines. However, these are not always satisfactory in view of the pharmaceutical effect and/or the harmful aftereffect thereof. Accordingly, diversified studies have been made in order to develop more excellent antitumor substances.

For instance, Bishop, J. H. reported that a certain kind of genetic products have a tyrosine-specific protein-kinase property (A. Rev. Biochem., 52, 301–354 (1983)). In addition, Cohen, S. et al. reported that a tyrosine-specific protein-kinase participates in the process of the propagation of cells by a variety of cell growth factors as a signal substance (J. Biol. Chem., 257, 1523–1531 (1982)) On the other hand, the present inventors screened, paying their attention to the said phenomena, inhibitors against tyrosine-specific protein-kinase activity widely from the natural world and found that a substance of the formula:

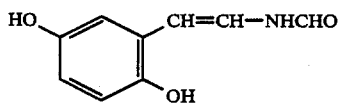

as produced by microorganisms belonging to the genus Streptomyces can inhibit the said protein-kinase activity in a low concentration and further has antimicrobial activity and antitumor activity. This was designated MH435-A and was already proposed (Refer to Japanese patent application No. 147039/85).

In addition, the present inventors formed a variety of MH435-A substance analogues by chemical synthesis in order to obtain compounds having a higher physiological activity and have found that some benzene compounds which are substituted by an isonitrilevinyl group, formamidovinyl group, formamidethylene group, lower alkanoylaminovinyl group or lower alkanoylaminoethylene group on the benzene ring and which are further nuclear-substituted by optionally protected hydroxyl group(s) or a halogen atom are in no way inferior to the above-mentioned MH435-A substance in the physiological activity and thus have achieved the present invention.

SUMMARY OF THE INVENTION

The present invention provides compounds of a general formula (I), which have an inhibitory activity against tyrosine-specific protein-kinase (hereinafter referred to as "TPK") and further have antimicrobial and/or antitumor activities:

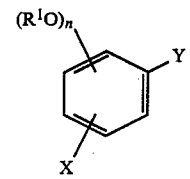

(in which $R^1$ represents a hydrogen atom, a lower alkanoyl group or a lower alkyl group; n represents a positive integer of 1 to 3;

X represents a hydrogen atom or a halogen atom;

Y represents a formula —CH=CH—NC, —CH=CH—NHR$^2$ or —CH$_2$—CH$_2$NHR$^2$ (where R$^2$ represents a formyl group or a lower alkanoyl group);

with the exception of the cases where X is hydrogen atom, $(R^1O)_n$ group is 2,5-dihydroxy group and Y is —CH=CH—NHCHO or —CH$_2$—CH$_2$NHCHO).

Accordingly, the present invention provides benzene compounds which are substituted by an isonitrilevinyl group, formamidovinyl group, formaidoethylene group, lower alkanoylaminovinyl group or lower alkanoylaminoethylene group on the benzene ring and which are further nuclear-substituted by optionally protected hydroxyl group(s) and/or a halogen atom.

DETAILED DESCRIPTION OF THE INVENTION

Among the above-mentioned compounds of the present invention, those having an isonitrilevinyl group not only have an especially strong antimicrobial activity but also are important as intermediates in synthesis of the compounds having a formamidovinyl group or formamidoethylene group. In the other compounds, those having a formamidovinyl group or lower alkanoylamidovinyl group are characterized by the strong inhibitory activity against TPK(hereinafter referred to as "TPK-I") and the strong antitumor activity.

In the present invention, the lower alkanoyl group and the lower alkyl group mean that the alkyl group part is an optionally branched alkyl group having 1 to 5 carbon atoms. Typical examples of these groups are acetyl, propionyl, n-butyryl, iso-butyryl, t-butyryl, pentanoyl, methyl, ethyl, propyl, iso-propyl, n-butyl, iso-butyl and pentyl groups.

Among these groups, acetyl group and methyl group are especially preferred as the protective group of the hydroxyl group. However, the compounds having free hydroxyl group(s) are desired in view of the activity in vitro.

The number of the substituents of the said hydroxyl groups may be 1 to 3. In particular, the compounds having two hydroxyl substituents, or that is, di-hydroxyl-substituted compounds are preferred.

The N-acyl group is significant in the point of the elevation of the stability of the compounds of the present invention, and the selection of the said group is not limitative since the preferred one is to be determined, depending upon the kind of the basic structure of the compounds. However, the hydroxyl group(s) on the aromatic nucleus is(are) preferably free also in the N-acyl derivatives because of the same reason as above.

The halogen atom includes anyone of fluorine, chlorine, bromine and iodine atoms, and in particular, the bromine atom-substituted compounds are especially preferred.

Typical examples of the compounds of the formula (I), which are preferred in the present invention, are given below.

(2-isonitrilevinyl)-2,5-dihydroxybenzene,
(2-isonitrilevinyl)-2,3-dihydroxybenzene,
(2-isonitrilevinyl)-2,4-dihydroxybenzene,
(2-isonitrilevinyl)-2,6-dihydroxybenzene,
(2-isonitrilevinyl)-3,4-dihydroxybenzene,
(2-isonitrilevinyl)-3,5-dihydroxybenzene,
(2-isonitrilevinyl)-2,5-dimethoxybenzene,
(2-isonitrilevinyl)-2,5-diacetoxybenzene,
(2-isonitrilevinyl)-2-hydroxy-3-methoxybenzene,
(2-isonitrilevinyl)-2-dihydroxybenzene,
(2-isonitrilevinyl)-2-hydroxy-3-bromobenzene,
(2-isonitrilevinyl)-2,3,4-trihydroxybenzene,
(2-isonitrilevinyl)-2,4,5-trihydroxybenzene,
(2-isonitrilevinyl)-2,3,5-trihydroxybenzene,
(2-isonitrilevinyl)-2,3,6-trihydroxybenzene,
(2-isonitrilevinyl)-3,4,5-trihydroxybenzene, and further, 2-formamidovinyl, 2-formamidoethylene or 2-alkanoylaminovinyl derivatives corresponding to the said compounds, with the exception of (2-formamidovinyl)-2,5-dihydroxybenzene and (2-formamidoethyl)-2,5-dihydroxybenzene.

Next, the compounds of the present invention can be obtained by reacting a compound of a formula (II):

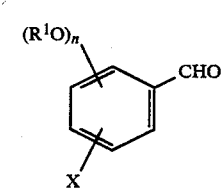

(in which $R^1$, n and X have the same meanings as mentioned above) and a diethyl isocyanomethyl-phosphite of a formula (III):

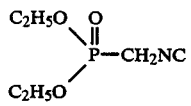

in the presence of a base, by a per se known Wittig reaction, optionally followed by acid hydrolysis and further hydrogenation of the resulting product.

The said Wittig reaction may be carried out for several hours at about $-78°$ C. to $0°$ C. in the presence of a substantially inactive polar solvent such as N,N-dimethylformamide, diethylether, dioxane or tetrahydrofuran (hereinafter referred to as "THF").

The reaction is preferably carried out in a water-free system; and as the base substance can be used a metal base such as sodium bis(trimethylsilyl)amide, sodium hydride, butyl lithium, potassium t-butoxide, etc.

By the said reaction are obtained the compounds of a formula (I-a), which fall within the scope of the compounds of the present invention:

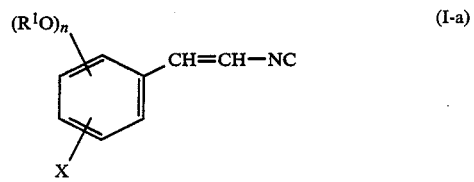

(in which $R^1$, n and X have the same meanings as given above). The compounds of the said formula (I-a) are, after isolated or not isolated from the reaction mixture in a conventional manner, subjected to acid-hydrolysis to give the compounds of a formula (I-b), which also fall within the scope of the compounds of the present invention.

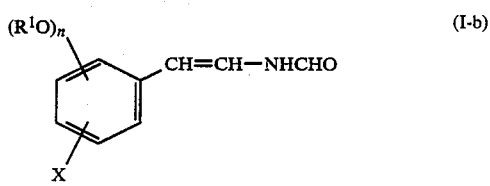

(in which $R^1$, n and X have the same meanings as given above).

The said hydrolysis reaction can be carried out in the co-presence of an organic solvent, such as ethyl acetate, diethylether, benzene, methyl alcohol, ethyl alcohol, THF, dioxane or chloroform, and water, using a catalyst of an organic acid, such as trifluoroacetic acid, acetic acid, oxalic acid or malonic acid, or an inorganic acid, such as hydrochloric acid, sulfuric acid or phosphoric acid, under the condition of about $-10°$ C. to $40°$ C. The reaction time is not critical but varies, depending upon the solvent and acid catalyst used and the reaction temperature. In general, the reaction may be completed in several hours to several days.

Further, the compounds of the formula (I-b) can be hydrogenated in the presence of a catalyst to give the other compounds of a formula (I-c), which also fall within the scope of the present invention:

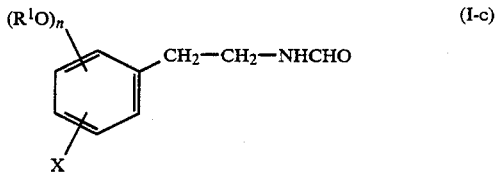

(in which $R^1$, n and X have the same meanings as given above).

The hydrogenation can be carried out by a per se known reaction which is generally used for the hydrogenation of an ethylene chain. For instance, the compound of the formula (I-b) is reacted with a hydrogen in the presence of a catalyst such as platinum oxide or palladium-carbon, using a solvent of a lower alkanol, such as methyl alcohol, ethyl alcohol or isopropyl alcohol, or water.

The compounds of the present invention as obtained in each of the above-mentioned steps can be isolated by a per se known isolation and purification method. For instance, the isolation can rationally be carried out by chromatography with silicagel.

In addition, the compounds of the formula (I-b) or (I-c) where $R^1$ is a lower alkanoyl group or a lower alkyl group can be converted into the corresponding N-acyl derivatives, which fall the scope of the compounds of the present invention, in accordance with the following reaction procedure. Reaction process:

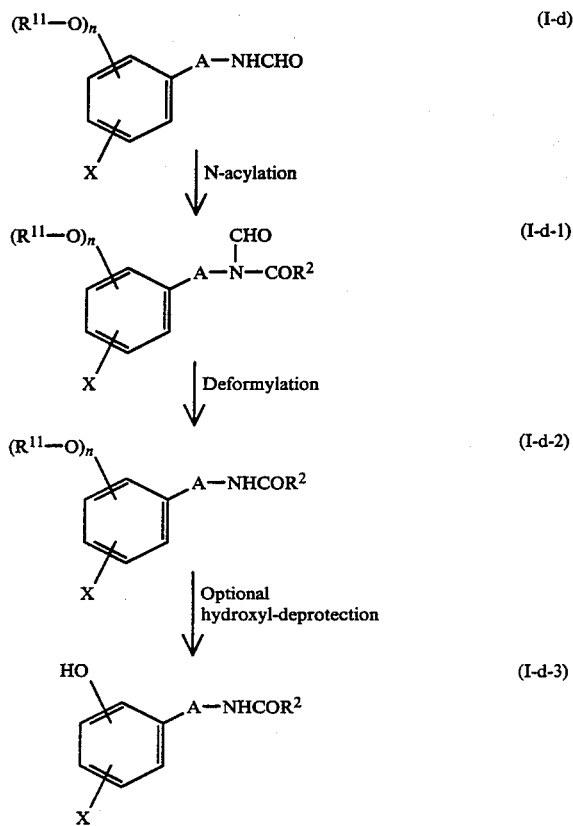

In the same reaction formulae, $R^{11}$ represents a lower alkanoyl group or a lower alkyl group; A represents a formula —CH=CH— or —CH$_2$—CH$_2$—; and $R^2$, X and n have the same meanings as given above.

The reaction in each reaction step of the abovementioned reaction procedure is carried out in accordance with a per se known method, which is concretely as follows:

(i) N-acylation:

This reaction is completed by reacting the compound of the formula (I-d) and an acylating agent such as a lower fatty acid, an acid anhydride or an acid halide. The reaction can be carried out by means of a per se known acylation method, for example, in the presence of a basic substance or the like.

(ii) Deformylation:

The reaction in this step is one to remove the N-formyl group from the compound of the formula (I-d-1), which can be carried out by means of a per se known deformylation method. For instance, the compound is treated with an inorganic acid such as hydrochloric acid or sulfuric acid in a solvent of a lower alcohol such as methanol or ethanol, at room temperature for several hours.

(iii) Hydroxyl-deprotection:

The reaction in this step is to selectively remove the lower alkanoyl group of the phenollic hydroxyl group in the compound of the formula (I-d-2), which can be carried out in the same manner as the above-mentioned step (ii) with the exception that the concentration of the acid used is elevated.

In each of the above-mentioned reaction steps, the isolation and purification of the product from the reaction mixture can be carried out by means of a per se known chromatography, solvent extraction of the like method.

The compounds of the present invention thus obtained have significant physiological activities, as mentioned hereinafter, and thus, these are useful as biochemical reagents, antimicrobial substances or antitumor substances.

Specifically, the effects of the compounds of the present invention are illustrated below.

(A) TPK-I activity:

The tyrosine-specific protein-kinase activity was assayed by means of a modified method of ELISA by G. Carpenter, et al. [(The Journal of Biological Chemistry, 254, 4874–4891 (1979)], where a membrane fraction of human epidermal carcinoma cells A-431 was used as the tyrosine-specific protein-kinase activator of an epidermal growth factor receptor Specifically, 1mM $MnCl_2$, 100 ng epidermal growth factor, 40 μg A-431 membrane fraction, 7.5 μg albumin, 3 μg histone and 50 μl of 20 mM Hepes buffer (pH 7.4) containing MH435-A or MH435-B were pre-incubated at 0° C. for 10 minutes, and 10 μl of ($\gamma$-$^{32}$P)-adenosine triphosphate (0.25 mCi/0.125 ml) was added thereto and reacted at 0° C. for 30 minutes. 50 μl of the reaction mixture was sampled and absorbed to Wattman No. 3MM filter membrane and dipped in an ice-cooled TCA. After kept for 30 minutes, the filter membrane was taken out and washed out TCA, ethanol and ether, and the count of $^{32}$P as stuck to the said filter membrane was measured (a). The same reaction and treatment were carried out, where the test substance only was excluded, and the count of $^{32}$P on the filter was measured in the same manner (b). Further, the values as measured in the cases where the membrane fraction was excluded were (a') and (b'), respectively. Thus, the percentage of the inhibition of the epiderman growth factor receptor-kinase was calculated from the formula of [(a−a')/(b−b')]×100.

The TPK-I activity of typical compounds of the present invention was extremely high at a low concentration, as shown in the following Table.

TABLE 1

| Compound No. | TPK-I IC$_{50}$ (μg/ml) |
|---|---|
| 1 | 6.25 |
| 2 | >6.4 |
| 3 | >10 |
| 9 | >6.4 |
| 10 | >30 |
| 11 | >6.4 |
| 12 | >100 |
| 13 | 0.3 |
| 14 | 1.3 |
| 18 | 3.0 |

(B) Growth inhibition activity against cultured carcinoma cells:

Each of L 1210 leukemia cells, IMC carcinoma cells, Ki-NRK, tsSre-NRK and A-431 cells were put on a dish (3–5×10$^4$ cells/dish) and incubated for one day (37° C., CO$_2$ concentration: 5%), and then, MH435-A was added thereto and further incubated for 3 days under the same condition. After the incubation, the number of the cells was counted and the activity was evaluated.

The 50%-inhibition concentration (IC$_{50}$) of typical compounds of the present invention against the growth of the said cells is given in the following Table, which indicates the usable effect of the compounds as a antitumor substance.

TABLE 2

| Compound No. | L 1210 IC$_{50}$ (μg/ml) |
| --- | --- |
| 1 | 1.4 |
| 2 | 0.25 |
| 3 | 0.65 |
| 9 | 12 |
| 10 | 62 |
| 11 | 23 |
| 12 | 30 |
| 13 | 2.2 |
| 14 | 22 |
| 18 | 3.0 |

(c) Antimicrobial activity:

The minimum growth inhibition concentration (MIC) of the compounds of the present invention against various bacteria was measured by means of an agar dilution method using Muller-Hinton medium, which is shown in the following Table.

TABLE 3

| | Tested Bacteria | |
| --- | --- | --- |
| Compound No. | Staphylococcus aureus Smith MIC (μg/ml) | Psudomonas aeruginosa A3 MIC (μg/ml) |
| 1 | 25 | 50 |
| 2 | 6.25 | 12.5 |
| 3 | 3.12 | 25 |
| 9 | 100 | >50 |
| 10 | >100 | >100 |
| 11 | >100 | >50 |
| 12 | >100 | >50 |
| 13 | 100 | 100 |
| 14 | >50 | 25 |

As shown in the above Tables, the compounds of the present invention have high PK-I activity, growth inhibition activity against cultured carcinoma cells and antimicrobial activity at a low concentration, and therefore, these are useful not only as biochemical reagents but also as antitumor agents and antimicrobial agents.

The present invention will be explained in greater detail by reference to the following examples, which, however, are not intended to be interpreted as limiting the scope of the present invention.

EXAMPLE 1

Preparation of 2-(2,5-dihydroxyphenyl)vinylisocyanide (1):

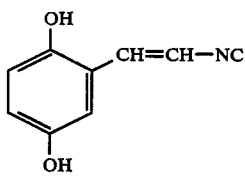

A solution of anhydrous tetrahydrofuran (THF) (2 ml) containing 132.8 mg of dimethyl isocyanomethyl-phosphite was dropwise added to a solution of anhydrous THF (2 ml) containing 137.3 mg of sodium bis(-trimethylsilyl)amide, while stirred at −78° C., under the substitution by nitrogen gas. The whole was stirred for 20 minutes at the same temperature, and then, a solution of anhydrous THF (1 ml) containing 20.7 mg of 2,5-dihydroxy-benzaldehyde was added thereto and reacted for 3 hours. Next, 100 μl of acetic acid was added, and the reaction mixture was diluted with 20 ml of ethyl acetate and washed with 0.1 M phosphate buffer (pH 7.0) for liquid-separation. The organic layer was dried with anhydrous sodium sulfate and concentrated under reduced pressure until the amount of the solvent became 3 ml, and thereafter, this was purified by preparative T.L.C. (toluene-acetone, 2:1) to obtain 14.0 mg of the said product (Yield: 59%).

Rf=0.17 (toluene-acetone, 2:1)

IR$\nu^{KBr}_{max}$ cm$^{-1}$: 3280, 2140, 1590, 1505

EXAMPLE 2

Preparation of 2-(5-bromo-2-hydroxyphenyl)vinylisocyanide (2):

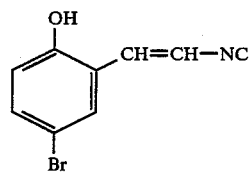

Using 342 mg of sodium bis(trimethylsilyl)amide, 331 mg of diethyl isocyano-phosphite and 149 mg of 5-bromo-2-hydroxybenzaldehyde, these were reacted and treated in the same manner as the Example 1. The crude product was purified by preparative T.L.C. (toluen-eacetone, 3:2), to obtain 106.8 mg of the said product (Yield: 65.0%).

Rf=0.69 (toluene-acetone, 3:2)

IR$\nu^{KBr}_{max}$ cm$^{-1}$: 3190, 2140, 1595, 1495

NMRδppm(CDCl$_3$):

5.52(1H,s);
6.55(1H,d, J=15 Hz);
6.70(1H,d, J=9 Hz);
7.02(1H,d, J=15 Hz);
7.35(1H,d, J=9 Hz);
7.40(1H,s).

EXAMPLE 3

Preparation of 2-(2,5-dimethoxyphenyl)vinylisocyanide (3):

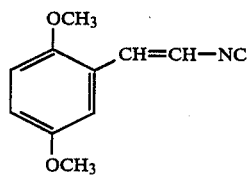

137.3 mg of sodium bis(trimethylsilyl)amide, 132.8 mg of diethyl isocyanomethyl-phosphite and 62 mg of 2,5-dimethoxybenzaldehyde were used, and these were reacted and treated in the same manner as the Example 1. The crude product was purified by preparative T.L.C. (toluene-ethyl acetate, 8:1), to obtain 44.5 mg of the said product (Yield: 63.0%).

Rf=0.73 (toluene-ethyl acetate, 8:1)

EXAMPLE 4

Preparation of 2-(2-hydroxy-5-methoxyphenyl)vinylisocyanide (4):

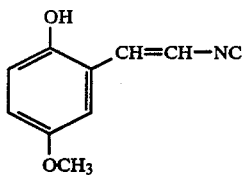

137.3 mg of sodium bis(trimethylsilyl)amide, 132.8 mg of diethyl isocyanomethyl-phosphite and 50 mg of 2-hydroxy-5-methoxybenzaldehyde were used, and these were reacted and treated in the same manner as the Example 1. After purified by preparative T.L.C. (toluene-acetone, 1:1), 38.2 mg of the said product was obtained (Yield: 67.0%).

RF=0.79 (toluene-acetone, 1:1)

EXAMPLE 5

Preparation of 2-(2-hydroxyphenyl)vinylisocyanide (5):

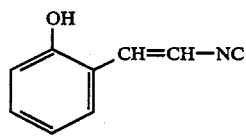

114 mg of sodium bis(trimethylsilyl)amide, 111 mg of diethyl isocyanomethyl-phosphite and 40 μl of 2-hydroxybenzaldehyde were used, and these were reacted and treated in the same manner as the Example 1. After purified by preparative T.L.C. (toluene-ethyl acetate, 8:1), 37.7 mg of the said product was obtained (Yield: 68.5%).

RF=0.44 (toluene-ethyl acetate, 8:1)

EXAMPLE 6

Preparation of 2-(2,3-dihydroxyphenyl)vinylisocyanide (6):

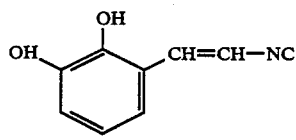

342 mg of sodium bis(trimethylsilyl)amide, 331 mg of diethyl isocyano-phosphite and 64.2 mg of 2,3-dihydroxybenzaldehyde were used, and these were reacted and treated in the same manner as the Example 1. After purified by preparative T.L.C. (chloroform-methanol, 10:1), 46.8 mg of the said product was obtained (Yield: 62.5%).

Rf=0.33 (chloroform-methanol, 10:1)

EXAMPLE 7

Preparation of 2-(3,4-dihydroxyphenyl)vinylisocyanide (7):

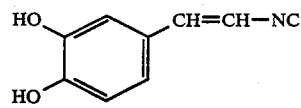

In the same manner as the Example 6 with the exception that 64.2 mg of 3,4-dihydroxybenzaldehyde was used, the materials were reacted and purified to obtain 49.0 mg of the said product (Yield: 65.5%).

Rf=0.46 (chloroform-methanol, 10:1)

EXAMPLE 8

Preparation of (2-formamidovinyl)2,5-dihydroxybenzene (8):

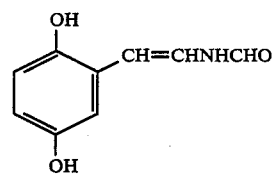

5 ml of 0.1 N hydrochloric acid-aqueous solution was added to 5 ml of ethyl acetate solution containing 10.0 mg of 2-(2,5-dihydroxyphenyl)vinylisocyanide and vigorously stirred for 2 days. The organic layer was washed with a saturated sodium chloride-aqueous solution and then, dried with anhydrous sodium sulfate, and the solvent was distilled out under reduced pressure. Next, the resulting residue was purified by preparative T.L.C. (toluene-acetone, 1:1), to obtain 4.7 mg of the said product (Yield: 42.4%).

Rf=0.37 (toluene-acetone, 1:1)

m.p.: 78°–82° C.

IR$\nu^{Kbr}_{max}$ cm$^{-1}$: 1650, 1540, 1510, 1400, 1320, 1260, 1200

NMR δppm(acetone-d$_6$):
6.64(1H,d, J=15.0 Hz);
6.51(1H,dd, J=3.0 Hz, 9.0 Hz);
6.68(1H,d, J=9.0 Hz);
6.80(1H,d, J=3.0 Hz);
7.63(1H,dd, J=15.0 Hz, J=11.0 Hz);
7.72(1H,s);
8.02(1H,s);
8.17(1H,s);
9.30(1H,br).

EXAMPLE 9

Preparation of (2-formamidovinyl)-5-bromo-2-hydroxybenzene (9):

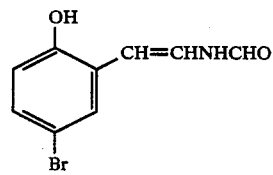

Using 20 mg of 2-(5-bromo-2-hydroxyphenyl)vinyl isocyanide, the materials were reacted and treated in the same manner as the Example 8. After purified by preparative T.L.C. (toluene-acetone, 3:2), 9.7 mg of the said product was obtained (Yield: 45%).

Rf=0.37 (toluene-acetone, 3:2)
m.p. 146.5°–148.0° C.
IR$\nu^{KBr}_{max}$ cm$^{-1}$: 3370, 3200, 1685, 1675, 1640, 1515, 1485, 1405
NMRδppm(acetone-d$_6$):
6.46(1H,d, J=15.0 Hz);
6.85(1H,d, J=9.0 Hz);
7.17(1H,dd, J=2.0 Hz, J=9.0 Hz);
7.48(1H,d, J=2.0 Hz);
7.90(1H,dd, J=9.0 Hz, J=15.0 Hz);
8.14(1H,s);
8.99(1H,s);
9.35(1H,br).

EXAMPLE 10

Preparation of (2-formamidovinyl)-2,5-dimethoxybenzene (10):

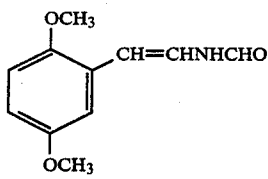

Using 20.0 mg of 2-(2,5-dimethoxyphenyl)-vinylisocyanide, the materials were reacted and treated in the same manner as the Example 8. After purified by preparative T.L.C. (toluene-acetone, 1:1), 10.1 mg of the said product was obtained 9Yield: 46.5%).

Rf=0.58 (toluene-acetone, 1:1)
m.p.: 83.5°–85.0° C.
IR$\nu^{KBr}_{max}$ cm$^{-1}$: 3300, 1710, 1685, 1665, 1530, 1510, 1230
NMRδppm(CDCl$_3$): 3.78(s), 3.81(s), 3.82(s), 6.23(d,J=15.0 Hz), 6.43(d,J=15.0 Hz), 6.79(s), 6.93(d,J=3.0 Hz), 8.22(s)

EXAMPLE 11

Preparation of (2-formamidovinyl)-2-hydroxy-5methoxybenzene (11):

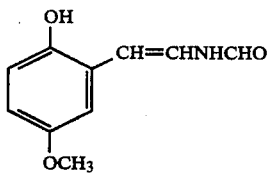

Using 30 mg of 2-(2-hydroxy-5-methoxyphenyl)-vinylisocyanide, the materials were reacted and treated in the same manner as the Example 8. After purified by preparative T.L.C. (toluene-acetone, 1:1), 13.7 mg of the said product was obtained (Yield: 41.3%).

Rf=0.50 (toluene-acetone, 1:1)
m.p.: 127.5°–129.0° C.
IR$\nu^{KBr}_{max}$ cm$^{-1}$: 3290, 3200, 1695, 1655, 1520, 1445, 1225
NMRδppm(CDCl$_3$+acetone-d$_6$): 3.76(3H,s);
6.50(1H,d, J=15.0 Hz);
6.61(1H,dd, J=3.0 Hz, J=9.0 Hz);
6.82(1H,d, J=9.0 Hz);
6.88(1H,d, J=3.0 Hz);
7.70(1H,s);
7.72(1H,d, J=15.0 Hz);
8.22(1H,s);
8.92(1H,br);

EXAMPLE 12

Preparation of (2-formamidovinyl)-2-hydroxybenzene (12):

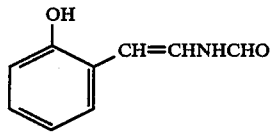

25 mg of 2-(2-hydroxyphenyl)vinylisocyanide was used, and the materials were reacted and treated in the same manner as the Example 8. After purified by preparative T.L.C. (toluene-ethyl acetate, 3:1), 13.6 mg of the said product was obtained (Yield: 48.5%).

Rf=0.12 (toluene-ethyl acetate, 3:1)
m.p.:118.0°–119.0° C.
IR$\nu^{KBr}_{max}$ cm$^{-1}$: 3350, 3200, 1660, 1645, 1640, 1530, 1455, 1385, 1255
NMRδppm(CDCl$_3$+acetone-d$_6$):
6.50(1H,d, J=15.0 Hz);
6.82(1H,dt, J=2.0 Hz, J=8.0 Hz);
6.88(1H,dd, J=2.0 Hz, J=8.0 Hz);
6.98(1H,dt, J=2.0 Hz, J=8.0 Hz);
7.32(1H,dd, J=2.0 Hz, J=8.0 Hz);
7.72(1H,dd, J=15.0 Hz, J=11.0 Hz);
8.01(1H,br);
8.21(1H,br);
8.60(1H,br).

EXAMPLE 13

Preparation of (2-formamidovinyl)-2,3-dihydroxybenzene (13):

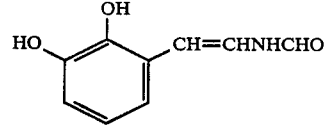

25 mg of 2-(2,3-dihydroxyphenyl)vinylisocyanide was used, and the materials were reacted and treated in the same manner as the Example 8. After purified by preparative T.L.C. (chloroform-methanol, 10:1), 12.2 mg of the said product was obtained (Yield: 44.2%).

Rf=0.12 (chloroform-methanol, 10:1)
UVλ$^{MeOH}_{max}$ nm (δ): 282(18600);
225(14500);
207(12000).
IR$\nu^{KBr}$max cm$^{-1}$: 3350, 1670, 1655, 1485, 1390, 1290
NMRδppm(acetone-d$_6$):
6.51(1H,d, J=15.0 Hz);
6.6–7.0(3H,m);
7.70(1H,dd, J=15.0 Hz, J=10.5 Hz);
8.22(1H,s);
7.60(1H,br);
8.50(1H,br);
9.25(1H,br);

EXAMPLE 14

Preparation of (2-formamidovinyl)-3,4-dihydroxybenzene (14):

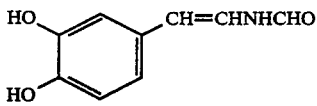

25 mg of 2-(3,4-dihydroxyphenyl)vinyl socyanide was used, and the materials were reacted and treated in the same manner as the Example 8. After purified by preparative T.L.C. (chloroform-methanol, 10:1), 15.8 mg of the said product was obtained (Yield: 46.3%).
Rf=0.29 (chloroform-methanol, 10:1)
m.p.:183°–187° C.
IR$\nu^{KBr}_{max}$ $cm^{-1}$: 3340, 3150, 1670, 1640, 1600, 1500, 1390, 1280, 1200
NMRδppm(acetone-d$_6$):
6.20(1H,d, J=15.0 Hz);
6.7–6.9(3H,m);
7.35(1H,d, J=15.0 Hz);
8.19(1H,s);

EXAMPLE 15

Preparation of (2-formaidoethyl)-2,3-dihydroxybenzene (15):

5 mg of platinum oxide was added to methanol solution (2 ml) containing 4.5 mg of (2-formamidovinyl)-2,3-dihydroxybenzene and stirred for 2 hours in hydrogen atmosphere. After the catalyst was filtrated out, the reaction solution was concentrated under reduced pressure, and the residue was purified by preparative T.L.C. (toluene-acetone, 1:1) to obtain 4.2 mg of the said product (Yield: 92.3%).
Rf=0.35 (toluene-acetone, 1:1)
NMRδppm(acetone-d$_6$-methanol-d4):
2.82(2H,t);
3.48(2H,t);
6.5–6.9(3H,m);
8.15(1H,s).

EXAMPLE 16

Preparation of (3-aza-3-formyl-4 oxopentenyl)-2,5-diazetoxy benzene (16):

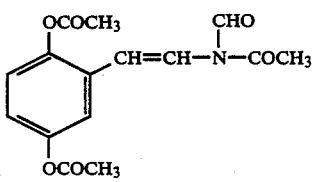

10 ml of acetic anhydride, 30 ml of triethylenamin and 5 mg of 4-dimethylaminopyridine were added to 2 ml of anhydrous methylene chloride-solution containing 14 mg of (2-formamidovinyl)-2,5-diacetoxybenzene and stirred for 4 hours at room temperature, and then, the reaction mixture was put into 20 ml of ethyl acetate and subjected to liquid-separation with 0.01N-hydrochloric acid and saturated sodium chloride-aqueous solution, and then, washed. The organic layer was dried with anhydrous sodium sulfate, and the solvent was distilled out under reduced pressure. The resulting residue was purified by preparative T.L.C. (toluene-acetone, 2:1) to obtain 15.0 mg of the said product (Yield: 92%).
Rf=0.82(chloroform-methanol, 10:1)
NMRδppm(CDCl$_3$):
2.28(3H);
2.32(3H,s);
2.43(3H,s);
6.9–7.3(5H,m);
9.30(1H,s).

EXAMPLE 17

Preparation of (2-acetamidovinyl)-2,5-diacetoxybenzene (17):

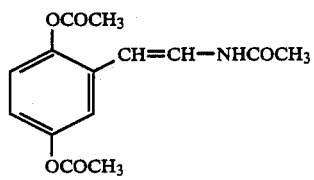

20 μl of 0.1 N-hydrochloric acid was added to 2 ml of methanol solution containing 15 mg of the compound (16) and stirred for 1 hour at room temperature. Next, 20 ml of ethyl acetate was added thereto and the resulting mixture was subjected to liquid-separation with saturated sodium chloride-aqueous solution and washed.
The organic layer was dried with anhydrous sodium sulfate, and then, the solvent was distilled out, and the residue obtained was purified by preparative T.L.C. (chloroform-methanol, 10:1) to give 12.5 mg of the said product (Yield: 91.7%).
Rf=0.53 (chloroform-methanol, 10:1)

EXAMPLE 18

Preparation of (2-acetamidovinyl)-2,5-dihydroxybenzene (18):

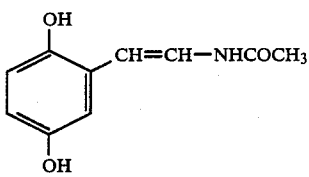

50 μl of 0.1N-hydrochloric acid was added to 2 ml of methanol solution containing 12.5 mg of the compound (17) and stirred for 4 hours at room temperature, and then, 30 ml of ethyl acetate was added thereto. The resulting mixture was subjected to liquid-separation with saturated sodium chloride-aqueous solution and washed.
The organic layer was dried with anhydrous sodium sulfate and then, the solvent was distilled out. The resulting residue was purified by preparative T.L.C. (chloroform-methanol, 10:1), to obtain 7.3 mg of the said product (Yield: 84%).
Rf=0.1 (chloroform-methanol, 10:1)
MNRδppm(acetone-d$_6$):
1.99(3H,s);
6 35(1H,d, J=15 Hz);
6.50(1H,dd, J=9 Hz, J=3 Hz);
6.70(1H,d, J=9 Hz);
6.82(1H,d, J=3 Hz);
7.60(1H,dd, J=15 Hz, J=10.5 Hz);

9.2(1H,br).

As apparent from the above description, the compounds of the present invention can inhibit the tyrosine-specific protein-kinase activity, and these are new substances which have excellent antimicrobial activity and antitumor activity. The present invention provides the new substances having the said valuable property.

What is claimed is:

1. A compound of the following formula:

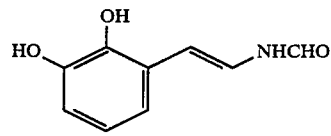

which is (2-formamidovinyl)-2,3-dihydroxybenzene.

2. A pharmaceutical composition comprising an effective amount of

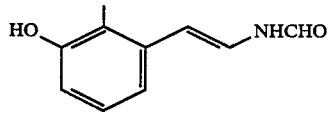

which is (2-formamidovinyl)-2,3-dihydroxybenzene in combination with a conventional pharmaceutical carrier or diluent.

* * * * *